(12) United States Patent
Sapian

(10) Patent No.: US 6,964,566 B2
(45) Date of Patent: Nov. 15, 2005

(54) ADJUSTABLE TOOTH SPREADING AND UPRIGHTING DEVICE

(76) Inventor: Schubert L. Sapian, 3412 Kingfisher La., Denton, TX (US) 76201

( * ) Notice: Subject to any disclaimer, the term of this patent is extended or adjusted under 35 U.S.C. 154(b) by 130 days.

(21) Appl. No.: 10/199,715

(22) Filed: Jul. 22, 2002

(65) Prior Publication Data

US 2004/0013996 A1     Jan. 22, 2004

(51) Int. Cl.$^7$ ................................................ A61C 7/00
(52) U.S. Cl. ........................................... 433/18; 433/21
(58) Field of Search ............................. 433/18, 19, 21, 433/24, 7

(56) References Cited

U.S. PATENT DOCUMENTS

| | | | | |
|---|---|---|---|---|
| 360,695 A | * | 4/1887 | Holmes | 433/7 |
| 678,452 A | * | 7/1901 | Angle | 433/12 |
| 3,525,153 A | * | 8/1970 | Gerber | 433/21 |
| 3,798,773 A | * | 3/1974 | Northcutt | 433/19 |
| 4,144,643 A | * | 3/1979 | Krygier | 433/7 |
| 4,200,979 A | * | 5/1980 | Wallshein | 433/7 |
| 5,531,594 A | * | 7/1996 | Cukjati | 433/1 |
| 5,564,920 A | * | 10/1996 | Klapper et al. | 433/7 |
| 5,738,514 A | * | 4/1998 | DeVincenzo et al. | 433/19 |
| 5,829,975 A | * | 11/1998 | Gold | 433/19 |
| 6,302,687 B1 | * | 10/2001 | King | 433/7 |
| 6,402,510 B1 | * | 6/2002 | Williams | 433/19 |
| 6,655,959 B2 | * | 12/2003 | Farzin-Nia et al. | 433/18 |
| 2001/0036614 A1 | * | 11/2001 | Farzin-Nia et al. | 433/7 |

* cited by examiner

Primary Examiner—Todd E. Manahan
(74) Attorney, Agent, or Firm—Morland C. Fischer

(57) ABSTRACT

An easy to install tooth spreading and uprighting device that is positioned on a temporary basis across an edentulous space between a pair of teeth in the mouth of a dental patient to correct and prevent the teeth from tipping and loosing their upright alignment which awaiting the implantation of a dental crown. The size of the tooth spreading and uprighting device is selectively adjustable depending upon the spacing between the patient's teeth so as to establish a tight fit and thereby apply a suitable holding pressure to prevent a misalignment of the teeth while awaiting the installation of the dental crown to replace a natural tooth which has been removed from the patient's mouth. The size of the tooth spreading and uprighting device is selectively adjustable by an inner body that is received within and slidable axially through a hollow outer body. An optional locking feature is provided to prevent a displacement of the inner body relative to the outer body.

15 Claims, 6 Drawing Sheets

ADJUSTABLE TOOTH SPREADING AND UPRIGHTING DEVICE

BACKGROUND OF THE INVENTION

1. Field of the Invention

This invention relates to an easy to install tooth spreading and uprighting device to be held across an edentulous space between a pair of teeth in the mouth of a patient to correct and preserve the upright alignment of the teeth prior to the implantation of a dental crown. The size of the tooth spreading and implanting device is selectively adjustable to establish a tight fit between the patient's teeth even in cases where more than a single tooth is missing or removed.

2. Background Art

One or more teeth in the mouths of dental patients are sometimes in need of removal as a consequence of periodontal disease, caries or decay, fractures, and trauma. With time, the posterior tooth or teeth from the edentulous site, tend to tip or lean forward or mesially, thereby reducing the edentulous space between the current or remaining teeth. By way of a particular example, when a molar or premolar tooth is pulled early in life, the distal molar or premolar tends to tip mesially over time, thereby closing the space or natural opening between the remaining teeth. For cosmetic purposes, as well as to prevent the neighboring teeth from loosing their upright alignment in the patient's mouth, a pontic crown is often installed within the edentulous area. Without the lateral support offered by a fixed or removable prosthetic device, the patient's teeth could undesirably tip, even within a relatively short time, which could result in jaw and other oral problems.

Once the patient's natural tooth is removed, it is usually preferable to install a dental implant immediately. However, depending upon the circumstance, it may be desirable to wait a reasonable time to permit the patient's gum tissue and bone structure to heal before beginning the process of installing a replacement tooth. That is to say, prior to drilling an implant socket into the patient's bone structure within which the root portion of a dental implant will be embedded, it is also preferable that the bone structure first be allowed to recover from its initial trauma. Such recovery time may take several months to a year, depending upon the health condition and the age of the patient and the size and number of natural teeth that have been removed. Accordingly, to prevent the patient's teeth from tipping towards the edentulous area and loosing their upright alignment, it would be desirable to have an easy to install, tooth spreading and uprighting device for use on a temporary basis as a chairside orthodontic appliance to extend across the evacuated space and between the patient's teeth to upright tipped teeth and prevent a further misalignment of the teeth while awaiting a replacement crown.

SUMMARY OF THE INVENTION

An easy to install tooth spreading and uprighting device is disclosed to be positioned on a temporary basis across an edentulous space between a pair of teeth in the mouth of a dental patient to upright tipped molars, or premolars and to prevent the teeth from tipping and losing their upright alignment while awaiting the implantation of a dental crown. The size of the tooth spreading and uprighting device is selectively adjustable depending upon the spacing between the patient's teeth so as to establish a tight fit and thereby apply a suitable holding pressure to prevent a misalignment of the teeth while awaiting the installation of the dental implant or other prosthetic dental device to replace a natural tooth which has been removed from the patient's mouth.

In a first embodiment, a hollow inner tube is received inwardly of and slidable axially through a hollow outer tube. Each of the inner and outer tubes has a flexible retainer affixed to one end thereof. The retainers have an arcuate shape and are adapted to be bent to conform to the shape of the patient's teeth. A coil spring is positioned within the hollow inner and outer tubes to exert an outward constant pushing force for holding the retainers against the respective teeth of the patient. That is, when the inner tube is moved inwardly towards the outer tube, the spring is compressed. The compressed spring pushes outwardly and in opposite directions against the inner and outer tubes to generate a self-adjusting holding pressure by which the tooth spreading and uprighting device is retained between the teeth of the patient. An optional locking pin extends laterally through the device for preventing a displacement of the inner tube relative to the outer tube for installation and space maintaining purposes.

In a second embodiment, a hollow rectangular inner body is received inwardly of and slidable axially through a hollow rectangular outer body. Each of the inner and outer bodies also has a flexible retainer affixed to one and thereof to engage and conform to the shape of the patient's teeth. A continuously folded or wave-shaped compression spring is positioned within the hollow inner and outer rectangular bodies to exert an outward pushing force thereagainst so as to generate a self-adjusting holding pressure by which the tooth spreading and uprighting device is retained between the teeth of the patient. A lip depending downwardly from an optional flexible arm carried by the outer body is received between a pair of ratchet teeth running along the inner body for preventing a displacement of the inner body relative to the outer body.

In a third embodiment, a coupling nut is received within a hollow tube. The coupling nut has a threaded channel running longitudinally therethrough. A threaded end of a cylindrical locking post is received within the threaded channel of the coupling nut so as to extend into and move axially through the hollow tube. Each of the hollow tube and cylindrical locking post also has a flexible retainer affixed to one and thereof to engage and conform to the shape of the patient's teeth. By applying a rotational force to the coupling nut, the locking post is caused to move outwardly from the hollow tube in a direction away from the coupling nut to thereby generate an adjustable holding pressure by which the tooth spreading and uprighting device is retained between the teeth of the patient.

DETAILED DESCRIPTION

Figure 1:
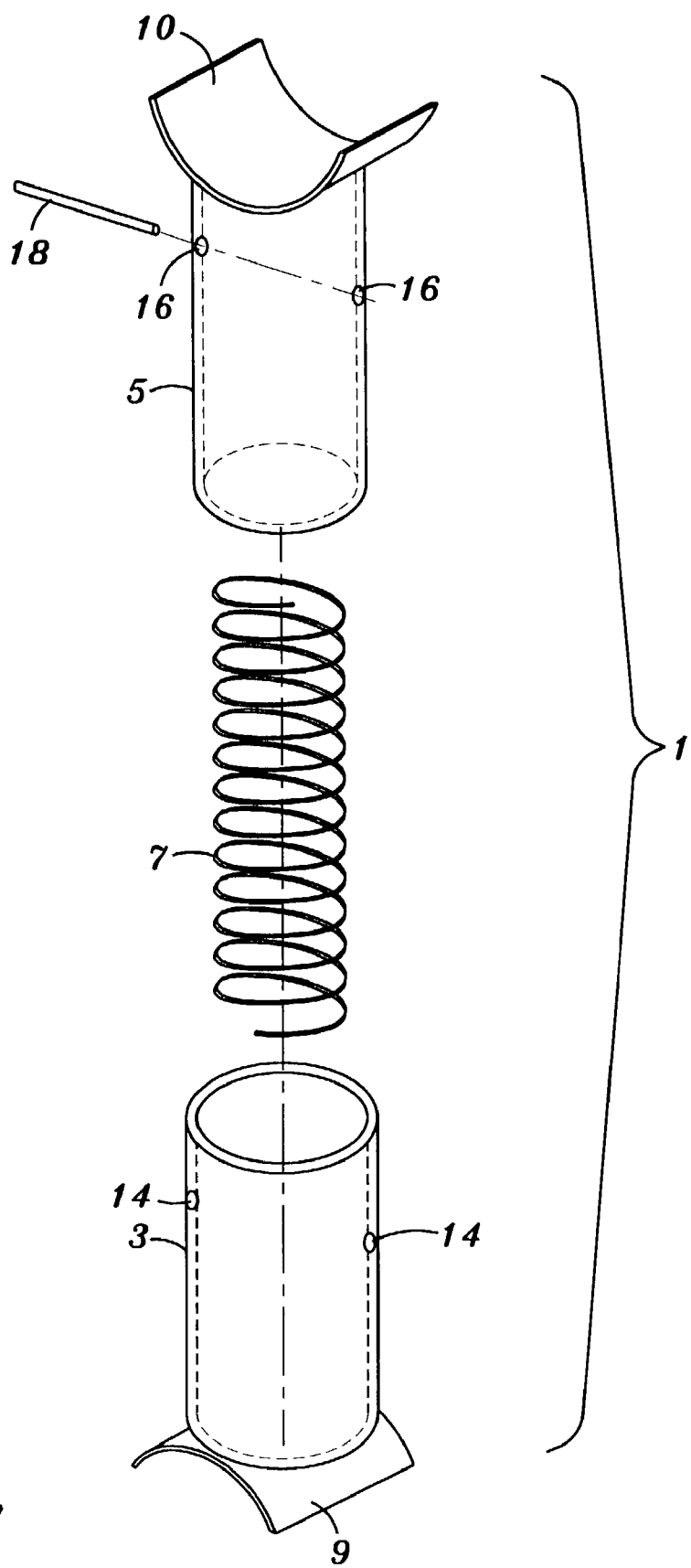
FIG. 1 is an exploded view showing a tooth spreading and uprighting device according to a first embodiment of this invention.

An easy to install, adjustable tooth spreading and uprighting device 1 which forms a first embodiment of this invention is initially described while referring to FIG. 1 of the drawings. As will be described in greater detail when referring to FIG. 4, the tooth spreading and uprighting device 1 is adapted to be reliably installed on a temporary basis across an edentulous space between a pair of teeth in the mouth of a patient to correct and preserve the upright alignment of the teeth prior to the implantation of a dental crown to replace a tooth which has been removed as a consequence of age, damage, disease, or the like.

The tooth spreading and uprighting device 1 includes first and second hollow tubes 3 and 5 having open front ends and closed rear ends. The tubes 3 and 5 are preferably manufactured from a biocompatible plastic or metallic material such as, for example, titanium or a titanium alloy or a flexible PVC. One of the hollow tubes 3 has a longer length and a larger diameter than the other tube 5. By way of example only, the first tube 3 has a length of 7.0 mm and an outside diameter of 5.0 mm. The second tube 5 has a length of 4.5 mm and an outside diameter of 4.0 mm. In the assembled relationship of FIGS. 2 and 3, the smaller second tube 5 is slidably received within the larger first tube 3.

Figure 2:
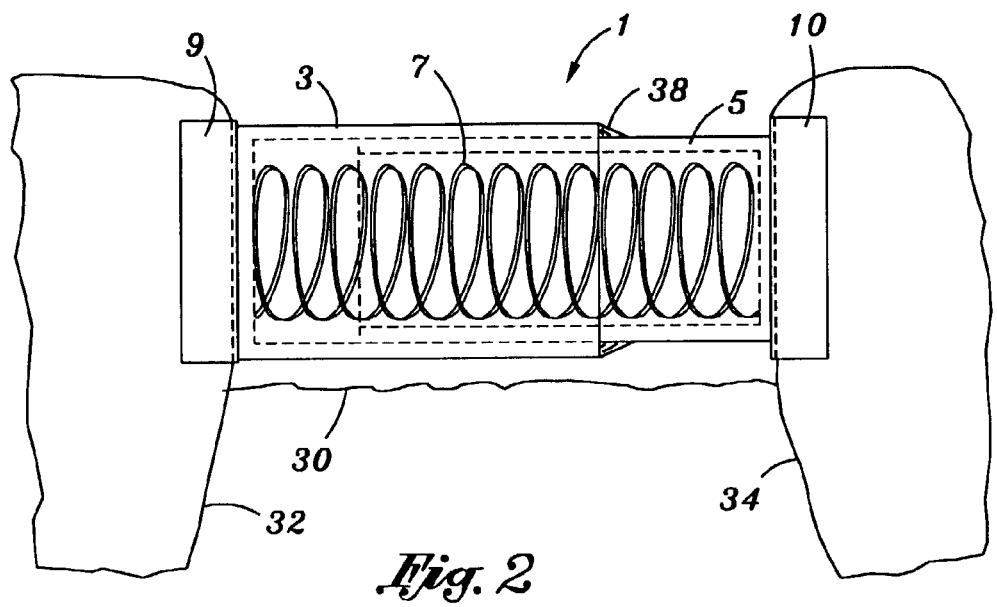
FIG. 2 is a side view of the tooth spreading and uprighting device of FIG. 1 installed between a pair of teeth of a dental patient.
Figure 3:
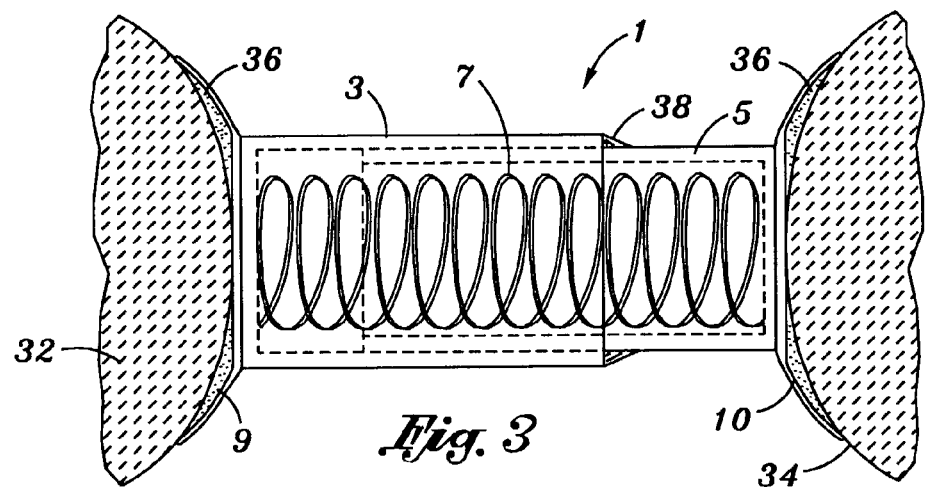
FIG. 3 is a top view of the tooth spreading and uprighting device of FIG. 1 installed between a pair of teeth of a dental patient.

More particularly, in the assembled configuration of FIGS. 2 and 3, the open front ends of the pair of hollow tubes 3 and 5 are arranged in opposing alignment with another, and a compression spring 7 is located therebetween. In this first embodiment, the spring is a coil spring 7 that is manufactured from a metallic material (e.g. nitinol nickel-titanium). The length of the coil spring 7 is selected to generate a constant spring pressure, which is sufficient to orthodontically displace a tooth or teeth held in bone.

A flexible retainer 9 and 10 is affixed (e.g. welded or composite bonded) to the closed rear end of each tube 3 and 5 of tooth spreading and uprighting device 1. The retainers 9 and 10 have a generally arcuate shape. As is best shown in FIGS. 2 and 3, the size of the arcuate retainers 9 and 10 is selected to conform to the size of the teeth between which the device 1 will be positioned. The flexible retainers 9 and 10 are preferably manufactured from either plastic, a ribbon fiber-glass material or a metallic material such as, for example, titanium or a titanium alloy mesh that is capable of being bent as well as welded to respective tubes 3 and 5.

As shown in FIGS. 2 and 3 of the drawings, the adjustable tooth spreading and uprighting device 1 is held in the assembled configuration across the space between a pair of the patient's teeth 32 and 34 with the smaller diameter tube 5 received inwardly of and slidable axially through the larger diameter tube 3 and the coil spring 7 compressed between the closed rear ends of tubes 3 and 5. In the case where the inner tube 5 is manufactured from a flexible plastic (e.g. PVC) material, the arcuate retainers 9 and 10 of tubes 3 and 5 are bonded to the sides of respective teeth 32 and 34 just above the patient's gum line 30 (best shown in FIG. 2). The compressed spring 7 within tubes 3 and 5 pushes outwardly and in opposite directions against the flexible retainers 9 and 10 so as to generate a self-adjusting holding pressure by which the spreading and uprighting device 1 is retained between teeth 32 and 34 regardless of the distance therebetween. In this regard, the flexible retainers 9 and 10 may be bent and shaped around teeth 32 and 34 on an as-needed basis to ensure a close mating engagement with each one of the patient's teeth.

It is preferable that the spreading and uprighting device 1 be bonded in place to prevent accidental dislodgement caused by eating or trauma, whereby to avoid an accidental swallowing. However, in cases where the patient's teeth 32 and 34 are spaced relatively far apart or where several teeth are missing, it may be desirable to include an additional locking feature to prevent a displacement of inner tube 5 relative to outer tube 3 and thereby reinforce the holding pressure that is created when the coil spring 7 pushes retainers 9 and 10 outwardly and into mating engagement with respective teeth 32 and 34 and the retainers 9 and 10 are bonded to the teeth.

By way of a first example, each of the flexible retainers 9 and 10 at the opposite ends of the spreading and uprighting device 1 may be bonded directly to the sides of the patient's teeth 32 and 34. More particularly, the retainers 9 and 10 can be affixed to the patient's teeth 32 and 34 by means of an optional composite bond (designated 36 and best shown in FIG. 3). What is more, once a suitable holding pressure is established by which the tooth spreading and uprighting device 1 is properly retained between the patient's teeth 32 and 34, the joint surrounding the small diameter inner tube 5 and the large diameter outer tube 3 can be sealed by an adhesive bond 38 (e.g. composite cement).

By way of a second example, and returning briefly to FIG. 1, pairs of pin holes 14 and 16 are formed through each of the outer and inner tubes 3 and 5 of the tooth spreading and uprighting device 1. In the assembled configuration (of FIGS. 2 and 3), when the inner tube 5 is slidably received by the outer tube 3, the pairs of pin holes 14 and 16 are axially aligned with one another. An optional locking pin 18 is inserted laterally through the outer and inner tubes 3 and 5 and past the coil spring 7 that is housed therewithin via the pairs of pin holes 14 and 16. The locking pin 18 is preferably manufactured from a medical grade stainless steel. Once the locking pin 18 is properly inserted in the spreading and uprighting device 1 (not shown), it may be cut to size and the pin holes 16 and 18 sealed. The presence of locking pin 18 prevents the outer and inner tubes 3 and 5 from sliding relative to one another so as to avoid an untimely separation thereof and a possible disassembly of device 1.

Figure 4:
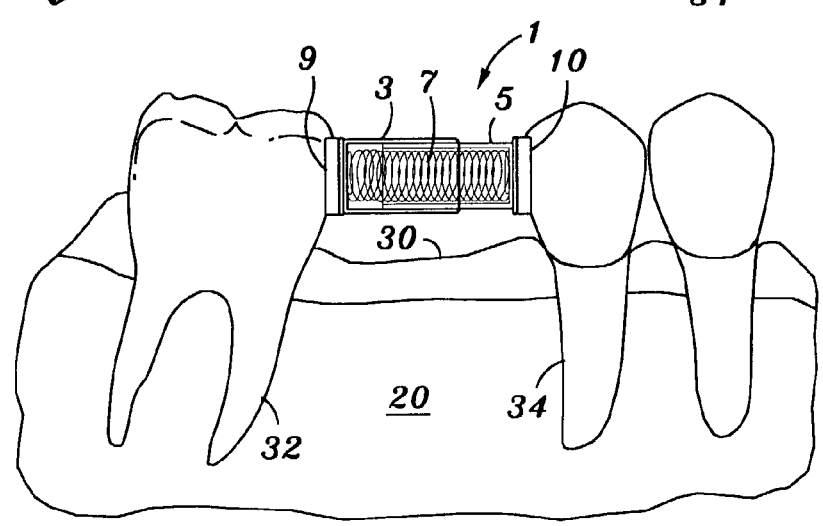
FIG. 4 is a perspective view of the tooth spreading and uprighting device of FIG. 1 installed between a pair of teeth of a dental patient.

Turning now to FIG. 4 of the drawings, there is shown the adjustable tooth spreading and uprighting device 1 of this first embodiment extending across the space between a pair of the patient's teeth 32 and 34 above the gum line 30. Typically, the spreading and uprighting device 1 will remain installed for about 30 to 60 days until proper spacing is achieved, during which time the patient's bone structure 20 and gum tissue can heal before a dental implant or bridge is installed. Depending upon the number of teeth which are missing from the patient's mouth and the corresponding distance between the teeth to be bridged or to receive an implant, the device 1 is capable of forming a brace of as long as 30 mm by selecting the sizes and adjusting the axially extended positions of the inner and outer hollow tubes 3 and 5 relative to one another. By virtue of the foregoing, a reliable, easy to install chairside device is available on a temporary basis to upright tipped posterior teeth and redeem the lost space therebetween to allow the placement of a dental prosthesis, such as a bridge, partial dentures, or dental implants.

Figure 5:
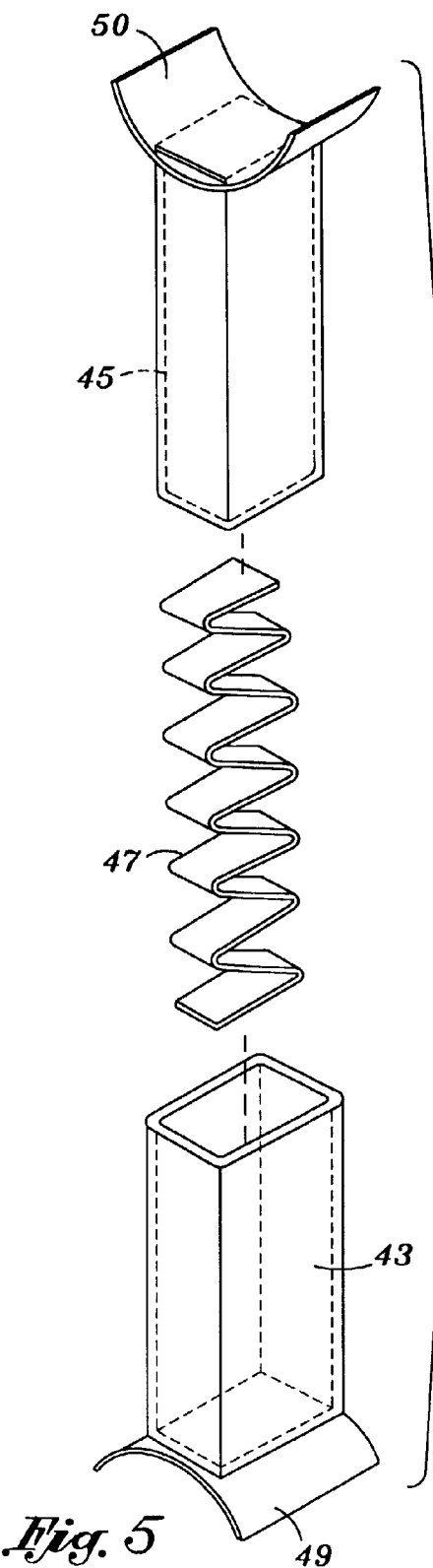
FIG. 5 is an exploded view showing a tooth spreading and uprighting device according to a second embodiment of this invention.

In the first embodiment of FIGS. 1–4, a tooth spreading and uprighting device 1 was illustrated having outer and inner hollow tubes 3 and 5 and a coil spring 7 surrounded thereby. FIG. 5 of the drawings shows a second embodiment of this invention where an adjustable tooth spreading and uprighting device 40 includes outer and inner hollow rectangular bodies 43 and 45 having opposite open and closed front and rear ends. The outer rectangular body 43 is characterized by a larger cross sectional area than the inner rectangular body 5 so that, in the assembled configuration (of FIG. 7), the inner body 45 is received within and slidable axially through the outer body 43. A compression spring 47 is located inwardly of the open front ends of the outer and inner hollow bodies 43 and 45. In this second embodiment, the compression spring 47 has a series of accordion-like folds so as to resemble a continuous wave. A flexible, arcuate-shaped retainer 49 and 50 is affixed (e.g. welded or bonded) to the closed rear end of each rectangular body 43 and 45. The assembly, installation and advantages of the tooth spreading and uprighting device 40 of this second embodiment will be described in detail hereinafter when referring to FIG. 7.

When describing the tooth spreading and uprighting device 1 of FIG. 1, an optional locking pin 18 was disclosed to be inserted laterally through the outer and inner tubes 3 and 5 to prevent a displacement of one tube relative to the other, whereby to reinforce its retention between the teeth and avoid an inadvertent disassembly of device 1 during installation. In this same regard, the spreading and uprighting device 40 of FIG. 5 may also be provided with an optional locking feature to reinforce the self-adjusting holding pressure that is created when the wave-like spring 47 pushes retainers 49 and 50 outwardly and into mating engagement with the patient's teeth (e.g. designated 32 and 34 in FIG. 7).

Figure 6:
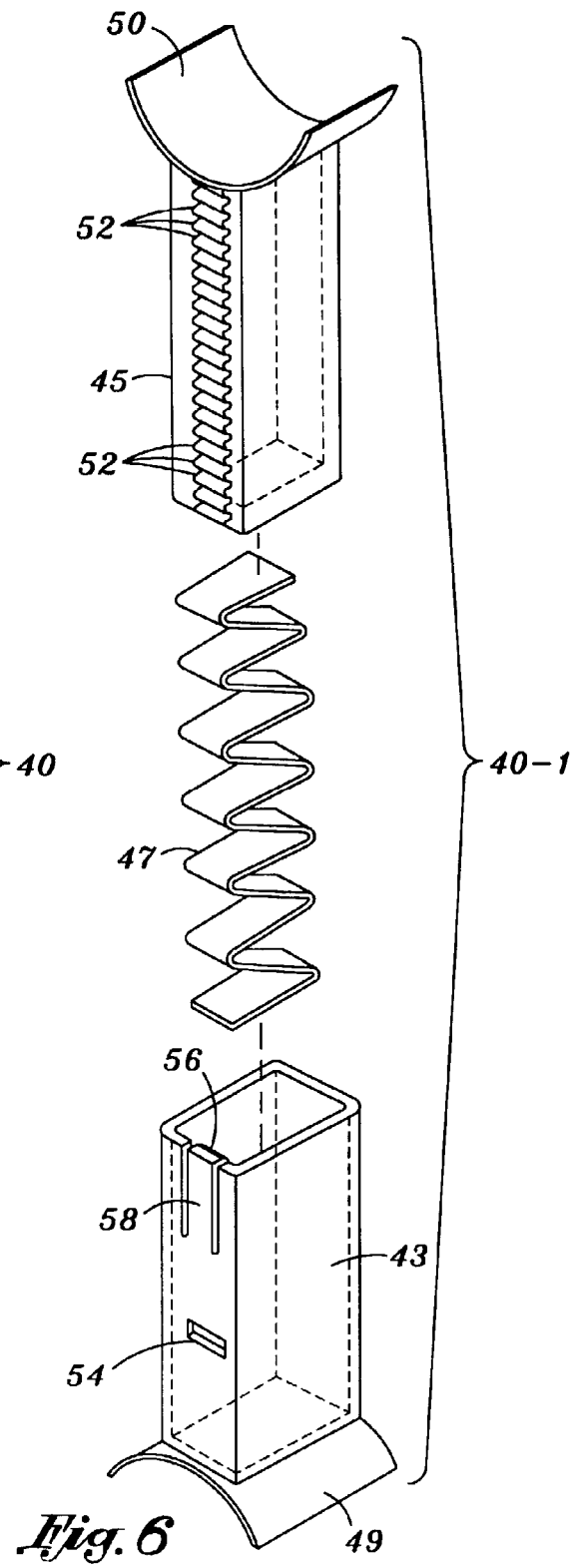
FIG. 6 shows an alternate embodiment of the tooth spreading and uprighting device of FIG. 5.

In this case, and referring now to the modified tooth spreading and uprighting device 40-1 of FIG. 6 of the drawings, the rectangular inner body 45 is provided with a series of ratchet teeth 52 running axially along the top thereof. The top of the rectangular outer body 43 of device 40-1 is provided with a slot or opening 54 and a lip 56. The lip 56 depends downwardly from a flexible arm 58 that is formed at the top of the outer body 43 so as to be received between a pair of the ratchet teeth 52 of inner body 45. The slot 54 through outer body 43 is sized and aligned for receipt therewithin of one of the ratchet teeth 52 of inner body 45.

Figure 7:
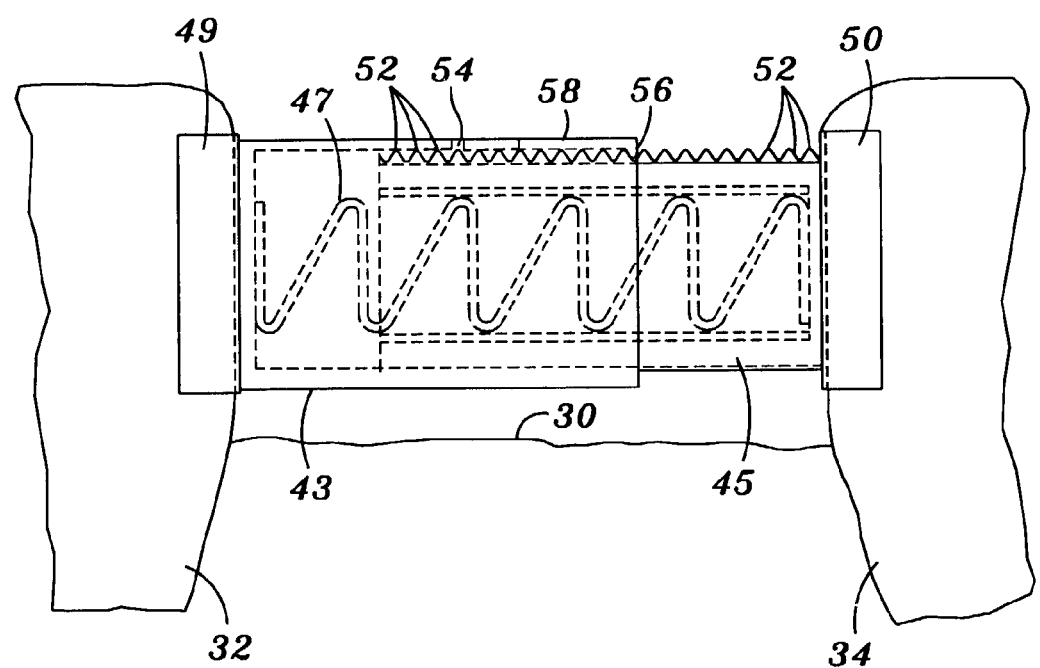
FIG. 7 is a side view of the tooth spreading and uprighting device of FIG. 6 installed between a pair of teeth of a dental patient.

FIG. 7 of the drawings shows the adjustable tooth spreading and uprighting device 40 of FIG. 6 retained across a space between a pair of the patient's teeth 32 and 34 with the rectangular inner body 45 moved inwardly of the rectangular outer body 43 such that the wave-like spring 47 is compressed between the closed rear ends of bodies 43 and 45. The arcuate retainers 49 and 50 of bodies 43 and 45 surround the pair of teeth 32 and 34 just above the patient's gum line 30. The compressed spring 47 pushes outwardly and in opposite directions against the flexible retainers 49 and 50 so as to generate a self-adjusting holding pressure by which the spreading and holding device 40 is retained between the patient's teeth 32 and 34.

However, in this case, once a suitable holding pressure is established, the lip 56 depending downwardly from the flexible arm 58 of outer body 43 is captured between a pair of the ratchet teeth 52 from inner body 45, and another one of the ratchet teeth 52 of inner body 45 is captured in the slot 54 formed in outer body 43. Hence, the tooth spreading and uprighting device 40 of FIGS. 6 and 7 will be reliably retained between the patient's teeth 32 and 34 with the rectangular outer and inner bodies 43 and 45 locked one within the other to prevent an inadvertent displacement and separation thereof.

Figure 8:
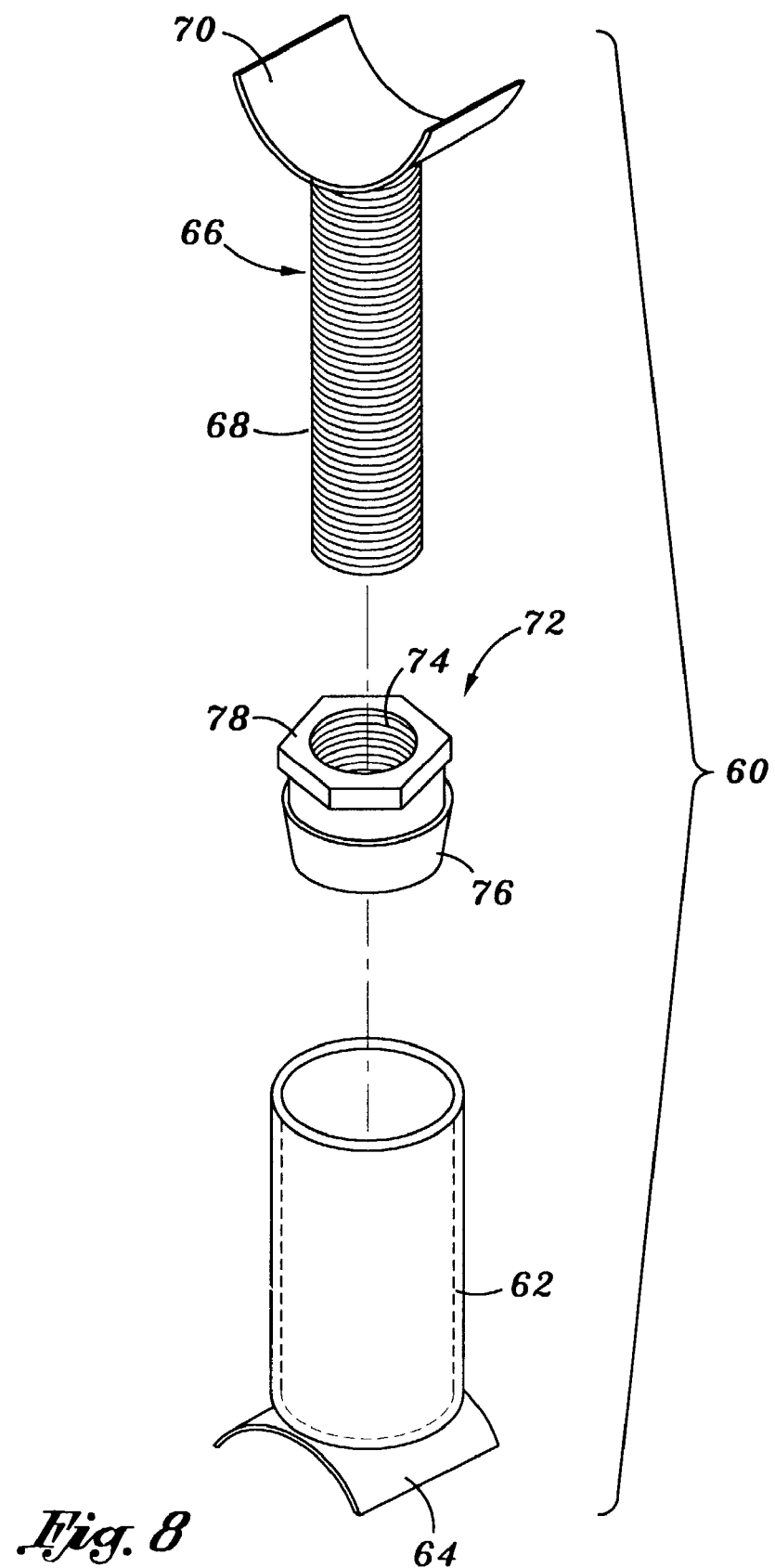
FIG. 8 is an exploded view showing a tooth spreading and uprighting device according to a third embodiment of this invention.

Each of the tooth spreading and uprighting devices that have heretofor been described while referring to FIGS. 1–7 includes a relatively small inner member that is received inwardly of and slidable axially through a relatively large outer member to cause a spring that is surrounded by the members to be compressed. In the embodiment of this invention shown in FIGS. 8 and 9 of the drawings, an adjustable tooth spreading and uprighting device 60 is shown that has neither slidable members nor a spring to be compressed thereby. In this case, device 60 includes a hollow outer tube 62 that is preferably manufactured from a biocompatible metallic or plastic material. The tube 62 includes an open front end and a closed rear end. A flexible, arcuate-shaped retainer 64 (similar to that shown in FIGS. 1–7) is affixed to the closed rear end of tube 62.

The tooth spreading and uprigthing device 60 also includes a cylindrical inner locking post 66 having a series of screw threads 68 extending circumferentially therearound. The cylindrical inner locking post 66 may have either a hollow or solid cross-section. However, the outside diameter of locking post 66 is less than the diameter of outer tube 62 so that locking post 66 is capable of moving back and forth through outer tube 62. Another flexible, arcuate retainer 70 is affixed to one end of the threaded inner locking post 66.

A metallic coupling nut 72 includes a screw threaded central channel 74 running longitudinally therethrough. A slightly tapered cylindrical body 76 is formed at one end of the coupling nut 72 and sized to be received within the open front end of the hollow outer tube 62. A hexagonal washer 78 is connected to cylindrical body 76 at the opposite end of the coupling nut 72. In the assembled configuration of FIG. 9, the cylindrical body 76 of the coupling nut 72 is loosely fit inside the open front end of the hollow outer tube 72 such that the relatively wide washer 78 is disposed outside outer tube 72 and in surrounding engagement with the front end thereof.

Figure 9:
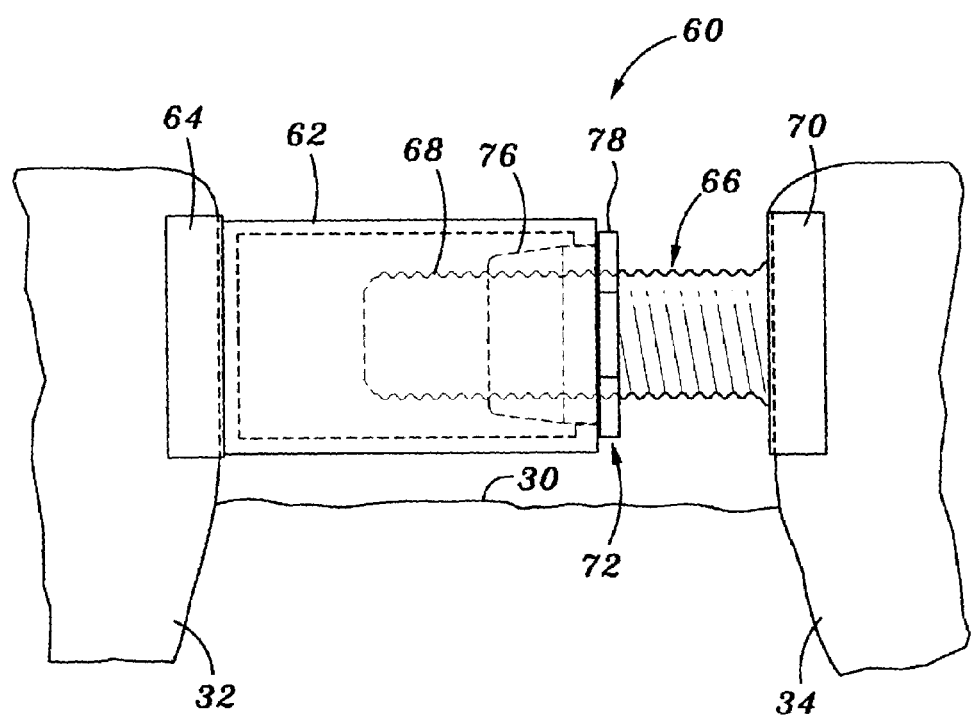
FIG. 9 is a side view of the tooth spreading and uprighting device of FIG. 8 installed between a pair of teeth of a dental patient.

More particularly, and referring to FIG. 9, the adjustable tooth spreading and uprighting device 60 is held in the assembled configuration across a space between a pair of the patient's teeth 32 and 34 with the coupling nut 72 located in the open front end of the hollow outer tube 62. The threaded end 68 of cylindrical locking post 66 is rotated into mating engagement with the nut 72 at the threaded central channel 64 thereof, whereby the threaded post 66 is coupled to outer tube 62 for axial movement therewithin. The opposing arcuate retainers 64 and 70 of tube 62 and locking post 66 surround the pair of teeth 32 and 34 just above the patient's gum line 30.

In the event that it is necessary to adjust the holding pressure by which the spreading and uprigthing device 60 is retained between teeth 32 and 34, a suitable wrench-like tool (not shown) is moved into contact with the hexagonal washer 78 of coupling nut 72. A rotational force applied to the tool applies a corresponding rotational force to the washer 78. Depending upon the direction in which the washer 78 is rotated, the threaded inner locking post 66 will either be moved axially outward and away from the hollow outer tube 62 to increase the holding pressure between the retainers 64 and 70 or axially inward towards the hollow outer tube 62 by which to decrease the holding pressure. Accordingly, the adjustable tooth spreading and uprighting device 60 of this embodiment can be easily installed and reliably retained between the patient's teeth 32 and 34. Other advantages of tooth spreading and uprighting device 60 are identical to those described above when referring to FIGS. 1–7 and, therefore, for purposes of convenience, will not be described again.

When the tooth spreading and uprighting devices of FIGS. 1–9 are installed, it may be desirable to prevent movement of the patient's remaining natural teeth by using bracing retainers, such as a composite wire splint or a plastic bite splint (often called an Essex retainer). In this regard, it is assumed that the patient still has a majority of his teeth in the arch so as to be able to use a wire splint or plastic bite splint for anchor support.

What is claimed is:

1. A spreading and uprighting device that is adapted to fit within an edentulous space between a pair of teeth in the mouth of a dental patient, and comprising:

a hollow outer body;

a hollow inner body being received within and slidable axially through said hollow outer body;

a compression spring disposed within said outer and inner hollow bodies, said compression spring having a compressed condition when said inner body slides inwardly through said outer body, and said compression spring having an expanded condition to exert a pushing force for causing said inner body to slide outwardly through said outer body, whereby to hold said outer and inner bodies against the pair of the patient's teeth so as to prevent a misalignment thereof, and a pair of flexible, generally U-shaped retainers respectively connected to opposite ends of said device at each of said hollow outer and inner bodies thereof and aligned relative to one another so as to be capable of engaging the opposing interproximal axial walls of respective ones of the pair of teeth at opposite ends of the edentulous space, said pair of flexible retainers being bent so as to conform to the shape of and surround the opposing interproximal axial walls of the pair of teeth between which said spreading and uprighting device is extended.

2. The spreading and uprighting device recited in claim 1, wherein each of said outer and inner bodies is a hollow cylinder and said compression spring is a coil spring.

3. The spreading and uprighting device recited in claim 1, wherein each of said outer and inner bodies has a hollow rectangular shape and said compression spring includes a series of folds running continuously therealong.

4. The spreading and uprighting device recited in claim 1, further comprising locking means by which to prevent said inner body from sliding axially through said outer body once said inner and outer bodies are held against the pair of the patient's teeth.

5. The spreading and uprighting device recited in claim 4, wherein said locking means includes a pin extending laterally through each of said hollow outer and inner bodies so as to prevent said inner body from being displaced relative to said outer body.

6. The spreading and uprighting device recited in claim 4, wherein said locking means includes an adhesive bond extending around the interface of said hollow outer and inner bodies so as to prevent said inner body from being displaced relative to said outer body.

7. The spreading and uprighting device recited in claim 4, wherein said locking means includes a flexible arm carried by said hollow outer body and a lip depending downwardly from said flexible arm and a series of ratchet teeth running along said hollow inner body, said flexible arm adapted to be bent towards said inner body, whereby said lip is moved into engagement with said inner body between a pair of said series of ratchet teeth running therealong so as to prevent said inner body from being displaced relative to said outer body.

8. The spreading and uprighting device recited in claim 7, wherein said locking means also comprises a slot formed in said hollow outer body and sized to receive therewithin one of said series of ratchet teeth running along said hollow inner body.

9. A spreading and uprighting device that is adapted to fit within an edentulous space between a pair of teeth from a row of teeth that is located at one side of the mouth of a dental patient, and comprising:

a hollow outer body to engage a first of the pair of teeth in the row of teeth at the said one side of the patient's mouth;

an inner body to engage the second of the pair of teeth in the same row of teeth at the said one side of the patient's mouth, said inner body being received by said hollow outer body;

a coupler received by said hollow outer body at the interior thereof by which to guide said inner body for movement through said outer body and axially relative to said row of teeth, said inner body moving outwardly through said outer body for causing said inner and outer bodies to be held against the pair of the patient's teeth so as to prevent a misalignment thereof; and a pair of flexible, U-shaped retainers respectively connected to opposite ends of said device at said hollow outer body and said inner body thereof and aligned relative to one another so as to be capable of engaging the opposing interproximal axial walls of respective ones of the pair of teeth at opposite ends of the edentulous space from the row of teeth located at the one side of the patient's mouth, said pair of flexible retainers being bent so as to conform to the shape of and surround the opposing interproximal axial walls of the pair of teeth between which said spreading and uprighting device is extended.

10. The spreading and uprighting device recited in claim 9, wherein said coupler is a nut having a channel running longitudinally therethrough, said inner body moving axially through said outer body by way of the channel running longitudinally through said coupler nut.

11. The spreading and uprighting device recited in claim 10, wherein the channel running longitudinally through said coupler nut has a series of screw threads extending therearound, said inner body having a corresponding series of screw threads by which said inner body is mated to said nut and aligned for axial movement therethrough.

12. The spreading and uprighting device recited in claim 11, wherein said hollow outer body is a cylindrical tube and said inner body includes a screw threaded cylindrical post received through the screw threaded channel running longitudinally through said coupler nut so as to move axially through said cylindrical tube in response to a rotational force applied to said coupler nut.

13. A spreading and uprighting device to extend across an edentulous space between a pair of teeth in the mouth of a dental patient, and comprising:
- a hollow outer body to engage a first of the pair of teeth,
- a hollow inner body to engage the second of the pair of teeth, said inner body being received within and slidable axially through said hollow outer body;
- a compression spring disposed within said outer and inner hollow bodies, said compression spring having a compressed condition when said inner body slides inwardly through said outer body, and said compression spring having an expanded condition to exert a pushing force for causing said inner body to slide outwardly through said outer body, whereby to hold said outer and inner bodies against the pair of the patient's teeth so as to prevent a misalignment thereof; and
- an adhesive bond located at the interface of said hollow outer and inner bodies so as to prevent said inner body from being displaced relative to said outer body.

14. A spreading and uprighting device to extend across an edentulous space between a pair of teeth in the mouth of a dental patient, and comprising:
- a hollow outer body to engage a first of the pair of teeth,
- a hollow inner body to engage the second of the pair of teeth, said inner body being received within and slidable axially through said hollow outer body;
- a compression spring disposed within said outer and inner hollow bodies, said compression spring having a compressed condition when said inner body slides inwardly through said outer body, and said compression spring having an expanded condition to exert a pushing force for causing said inner body to slide outwardly through said outer body, whereby to hold said outer and inner bodies against the pair of the patient's teeth so as to prevent a misalignment thereof;
- a flexible arm carried by one of said hollow outer body and said hollow inner body and a lip depending from said flexible arm; and
- a series of ratchet teeth running along the other one of said hollow outer body and said hollow inner body, said flexible arm adapted to bend to cause said lip depending therefrom to be moved into engagement with said series of ratchet teeth so as to prevent said inner body from being displaced relative to said outer body.

15. The spreading and uprighting device recited in claim 14, further comprising a slot formed in the one of said hollow outer body and said hollow inner body which carries said flexible arm, said slot being sized to receive therewithin one of said series of ratchet teeth running along the other one of said hollow outer and inner bodies.

* * * * *